(12) United States Patent
Saito

(10) Patent No.: US 8,419,187 B2
(45) Date of Patent: Apr. 16, 2013

(54) ADAPTIVE OPTICS APPARATUS THAT CORRECTS ABERRATION OF EXAMINATION OBJECT AND IMAGE TAKING APPARATUS INCLUDING ADAPTIVE OPTICS APPARATUS

(75) Inventor: Kenichi Saito, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 214 days.

(21) Appl. No.: 12/907,756

(22) Filed: Oct. 19, 2010

(65) Prior Publication Data

US 2011/0096292 A1    Apr. 28, 2011

(30) Foreign Application Priority Data

Oct. 23, 2009   (JP) .................................. 2009-244961

(51) Int. Cl.
*A61B 3/14* (2006.01)
*A61B 3/10* (2006.01)
*A61B 3/00* (2006.01)

(52) U.S. Cl.
USPC ............ 351/206; 351/205; 351/221; 351/246

(58) Field of Classification Search ........... 351/200–246
See application file for complete search history.

(56) References Cited

U.S. PATENT DOCUMENTS

| 2003/0076575 | A1 | 4/2003 | Stappaerts |
| 2003/0210378 | A1 | 11/2003 | Riza |
| 2006/0238710 | A1 | 10/2006 | Dick et al. |
| 2007/0076163 | A1 | 4/2007 | Crossland |
| 2007/0291230 | A1 | 12/2007 | Yamaguchi |
| 2008/0252900 | A1* | 10/2008 | Hatori ........................... 356/482 |
| 2011/0071402 | A1* | 3/2011 | Masumura .................... 600/476 |
| 2011/0096337 | A1* | 4/2011 | Hirose et al. .................. 356/491 |

OTHER PUBLICATIONS

Zawadzki, Robert J., et al.,"Adaptive-optics optical coherence tomography for high-resolution and high-speed 3D retinal in vivo imaging", Oct. 17, 2005 / vol. 13, No. 21 / Optics Express 8532.
XP002619392, L. Hu, et al, "A polarization independent liquid crystal adaptive optics system", Journal of Optics 2010, 045501, 6pgs.

* cited by examiner

*Primary Examiner* — Mohammed Hasan
(74) *Attorney, Agent, or Firm* — Canon U.S.A., Inc., IP Division

(57) ABSTRACT

An adaptive optics apparatus includes a first light modulating unit configured to perform modulation in a polarization direction of one of two polarized light components in light emitted from a light source, a changing unit configured to rotate the light modulated by the first light modulating unit by 90 degrees, a second light modulating unit configured to modulate the light changed by the changing unit in the polarization direction, and an irradiating unit configured to irradiate a measurement object with the light modulated by the second light modulating unit.

9 Claims, 4 Drawing Sheets

ADAPTIVE OPTICS APPARATUS THAT CORRECTS ABERRATION OF EXAMINATION OBJECT AND IMAGE TAKING APPARATUS INCLUDING ADAPTIVE OPTICS APPARATUS

BACKGROUND OF THE INVENTION

1. Field of the Invention

The present invention relates to an adaptive optics apparatus that corrects aberration of an examination object, and an image taking apparatus including an adaptive optics apparatus, and more specifically, it relates to a technique suitable for an optical image taking apparatus used, for example, for ophthalmic care and including an adaptive optics that corrects aberration of an eye.

2. Description of the Related Art

In an apparatus that is used, for example, for astronomical observation or fundus examination and measures an object using light, factors that lie between a measurement object and a detection optical system and fluctuate with time or vary greatly from individual to individual affect the imaging performance of the optical system and in some cases make it impossible to obtain sufficient resolution. These factors are caused, for example, by atmospheric fluctuation, change in a tear film of an eye, or individual difference in imperfection of an ocular optical system, include high-order optical aberration components, and are often not sufficiently corrected by an optical system including lenses and mirrors. A technique of an adaptive optics (hereinafter referred to as AO) is known that measures the changing aberration and feedback-controls the aberration using a device capable of dealing with high-order aberration.

In the case of fundus examination (in this case, the examination object is an eye), it is desirable to identify a photoreceptor cell unit on a retina, the size of which is of the order of magnitude of 2 to 3 μm. Ultimately, it is desirable to achieve an optical biopsy capable of cellular imaging in the near future. In order to achieve this, a spatial resolution of 1 μm or less comparable to a microscopical image of a piece of tissue is required. The wavelength of light used for such retina examination must be within the near infrared or infrared region in which light is poorly absorbed by water, which is the major component of the body tissue, and is poorly scattered in the tissue. In order to obtain a lateral resolution of 1 to 3 μm, the diameter of a beam incident on the pupil needs to be about 6 to 8 mm. Actually, in an optical system of an eye, from a cornea to a vitreous body, the state of the curved surface and the refractive index of each tissue are often not uniform. Even when an eye is observed with a beam having a diameter of about 6 to 8 mm, the wavefront of light is distorted in the eye, and a desired resolution cannot be obtained.

In Opt. Express 13, 8532 (2005) is reported a method to obtain desired light-collecting performance by using the AO technique, detecting aberration of a wavefront distorted in an eye, and compensating for the aberration with an aberration corrector. The AO in Opt. Express 13, 8532 (2005) employs a deformable mirror (hereinafter referred to as DM) including a wavefront aberration detector and 35 actuators. It is reported that an optical coherence tomography (hereinafter referred to as OCT) having such an adaptive optics achieved a resolution in the lateral direction of 4 μm and a resolution in the depth direction of 6 μm. In the case of such a DM, the optimal mirror shape to correct the aberration is formed by pushing and pulling a continuous surface mirror with several tens of actuators. Therefore, interaction between actuators occurs and complicates control calculation. Depending on the aberration shape, a desired shape cannot be sufficiently reproduced.

Japanese Patent Laid-Open No. 2007-014569 proposes an ophthalmic photographing apparatus including an AO having a wavefront aberration corrector that is a spatial light modulator (hereinafter referred to as SLM), which has superiority over a DM in wavefront reproducibility. The apparatus of Japanese Patent Laid-Open No. 2007-014569 is a scanning laser ophthalmoscope (hereinafter referred to as SLO) that scans a laser beam to obtain an fundus image. The SLO includes an AO that employs an SLM that uses orientational control of liquid crystal. Optical distance is the product of refractive index n and geometrical distance d. The above-described DM corrects a wavefront by changing d. In contrast, an SLM can correct wavefront aberration by changing n and thereby changing a wavefront. In the case, for example, of an SLM using liquid crystal, the number of pixels is very large, there is little interaction between pixels, and therefore control can be performed independently. Consequently, the SLM has superiority over the DM in wavefront reproducibility.

However, an AO that employs an SLM that uses orientational control of liquid crystal, such as that in Japanese Patent Laid-Open No. 2007-014569, has the following problems. When an SLM that uses orientational control of liquid crystal is used as in Japanese Patent Laid-Open No. 2007-014569, only light in a particular polarization direction is modulated. Therefore, when linearly polarized light (intrinsic polarized light) polarized in that direction is incident, ideally, 100% of incident light can be modulated. Therefore, when linearly-polarized laser or light from an SLD (Super Luminescent Diode) light source is incident on the SLM, high modulation efficiency can be achieved.

When such light is incident on the SLM, a polarized light component perpendicular to the modulation direction cannot be modulated, and outgoing light from the SLM includes two polarized light components that differ in spatial phase state (differ in wavefront). The component that is not the intrinsic polarized light of the SLM is not efficiently modulated, the wavefront cannot be sufficiently corrected, and therefore a desired resolution cannot be obtained. Disposing a polarizer that is parallel to the modulated polarization direction in front of the SLM makes it possible to select modulated light component. However, the polarized light component that is not modulated is removed, and therefore light use efficiency is significantly lowered. A retina has a low reflectivity, and the power of light illuminating it is limited by standards for safety. In the case of an examination object like a retina, it may be difficult to obtain a good-quality image when light quantity loss is about half.

SUMMARY OF THE INVENTION

In an aspect of the present invention, an adaptive optics apparatus includes a first light modulating unit configured to perform modulation in a polarization direction of one of two polarized light components in light emitted from a light source, a changing unit configured to rotate the light modulated by the first light modulating unit by 90 degrees, a second light modulating unit configured to modulate the light changed by the changing unit in the polarization direction, and an irradiating unit configured to irradiate a measurement object with the light modulated by the second light modulating unit.

The present invention can provide an adaptive optics apparatus capable of reducing the influence of the polarization state of incident light on the modulation characteristic, improving light use efficiency, and correcting aberration of an examination object even when a modulating unit (light modulating unit) that functions in a single polarization direction is employed, and an image taking apparatus including an adaptive optics apparatus.

Further features of the present invention will become apparent from the following description of exemplary embodiments with reference to the attached drawings.

DESCRIPTION OF THE EMBODIMENTS

Figure 2:
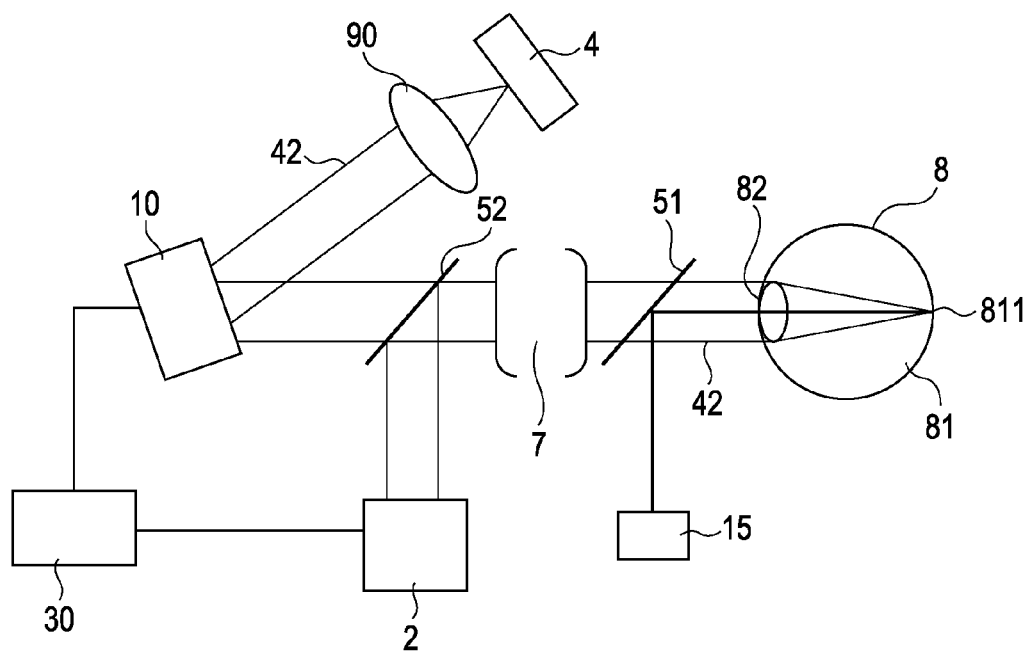
FIG. 2 is a conceptual diagram illustrating aberration correction with a fundus examination device including an adaptive optics including a wavefront aberration correction unit.

Next, an adaptive optics of the present invention that corrects the aberration of an examination object will be described with reference to the drawings. First, a configuration that corrects the aberration in the adaptive optics will be described with reference to FIG. 2. It is assumed that the adaptive optics is applied to a fundus camera. To obtain the information on a retina 81 of an eye 8 (examination object) noninvasively and optically, the retina 81 is irradiated with first illumination light (not shown), and reflected or scattered light from a measurement point 811 on the retina 81 is imaged onto a light receiving sensor 4 through an ocular optical system 8 and optical systems 7 and 90. The light receiving sensor 4 is an imaging element in which light receiving units are arranged in a matrix. In order to obtain optically high-resolution information, it is necessary to increase the size of the entrance pupil of the optical system 7 (corresponding to the position of the pupil 82). Due to the aberration of the ocular optical system, the wavefront of light 42 going out of the eye has aberration. When this light is imaged onto the light receiving sensor 4 by the optical systems 7 and 90, these optical systems do not provide their original imaging performance, and a distorted and enlarged spot is formed. Therefore, the spatial resolution in the lateral direction cannot be sufficiently obtained, and an image of a desired high resolution cannot be obtained.

The aberrations include low-order aberrations, such as astigmatism, defocus, and tilt, that can be corrected by an optical element such as a cylindrical lens and high-order aberrations, such as coma aberration and fourth-order spherical aberration. These aberrations are caused by distortion of curved surface or nonuniformity in refractive index of the anterior segment of the eye, such as a cornea or a lens. These factors vary greatly from individual to individual and include factors that change with time, such as the state of the tear layer on the surface of the cornea. In the adaptive optics (AO), these aberrations are measured by a wavefront aberration detector and are corrected by a wavefront aberration corrector. In the configuration of the AO of FIG. 2, the optical system has a wavefront aberration correction unit 10 disposed at a position optically conjugate to the entrance pupil (the pupil of the eye). A wavefront aberration detector (Shack-Hartmann sensor: HS sensor) 2 is disposed at another conjugate position on a branch formed by a branch member 52, such as an optical splitter. The wavefront aberration detector will hereinafter be referred to as HS sensor. A second light source 15 (a light source that emits light for aberration measurement) for detecting wavefront aberration is provided. Light from the light source 15 is incident on the eye 8 through a branch member 51 and is collected onto a measurement point 811 on the retina 81. A configuration such that light for aberration measurement is emitted from the vicinity of the eye can prevent stray light, for example, due to a lens of an optical system (intense reflected light near the center of a lens) from being detected by the wavefront sensor 2. When the diopter is zero, the reflected or backscattered light 42 from this point 811 is converted into substantially parallel light by an ocular optical system such as the cornea, passes through the branch member 51, is converted by the optical system 7 into a light beam having a predetermined diameter, is then reflected by the branch member 52, and is incident on the HS sensor 2.

Figure 3:
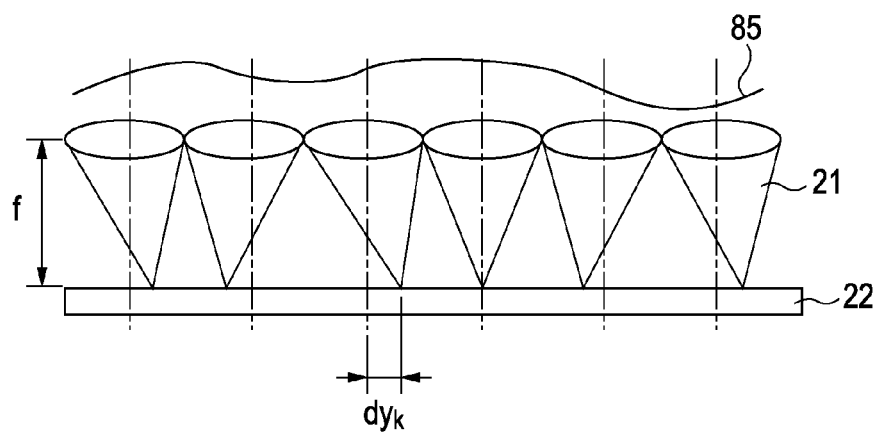
FIG. 3 is a principle diagram illustrating a wavefront aberration detector.

The principle of detection of the HS sensor 2 is illustrated in FIG. 3. Light having a wavefront 85 such as that shown in FIG. 3 and incident on the HS sensor 2 is caused to form spots on a two-dimensional light receiving element 22 by subapertures of lens elements of a microlens array 21 disposed at a position optically conjugate to the pupil. These spots each form an image, according to the gradient of the wavefront incident on the sub-aperture, at a position at a distance of $dy_k$ from the optical axis position (shown by chain line) of each microlens on the two-dimensional light receiving element 22. Let f denote the focal length of each microlens. The gradient $y_k$ of the wavefront is calculated by $y_k = dy_k / f$. By putting together the wavefront gradient calculated in each subaperture, the curved surface of the wavefront 85 is obtained in the form of W (x, y). The HS sensor 2 is optically conjugate to the wavefront aberration correction unit 10. Therefore, the wavefront in the wavefront aberration correction unit 10 has the same shape W (x', y'). In order to correct the wavefront of the reflected light from the wavefront aberration correction unit 10 and to make it a substantially plane wave, control is performed such that an aberration of —W (x', y') is given in the wavefront aberration correction unit 10. The above-described series of calculation and control is performed by a calculator 30.

The reflected or backscattered light 42 from the point 811 passes through the anterior segment 82 of the eye and the optical system 7, then the wavefront of the light 42 is corrected by the wavefront aberration correction unit 10, and the light 42 is imaged by the imaging lens 90 onto the light receiving sensor 4. If the wavefront aberration correction unit 10 is not driven, the light collection spot on the retina is a distorted and enlarged spot due to the aberration caused by the imperfection of the ocular optical system. Since the aberration is corrected by the wavefront aberration correction unit 10, light is collected to a spot according to a desired resolution. A DM is most commonly used as the wavefront aberration correction unit 10. However, in view of characteristic superiority, a reflective LCOS (Liquid Crystal on Silicon)—SLM is used here. However, as described above, an SLM that uses orientational control of liquid crystal is disadvantageous in that it can modulate only a polarized light component in a particular direction (intrinsic polarization direction).

Figure 4A:
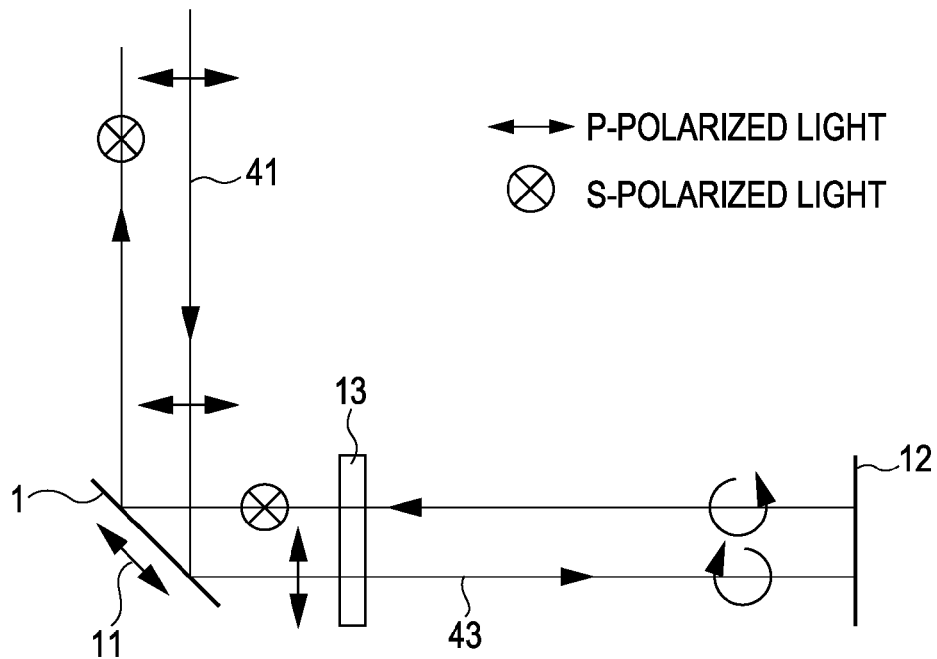
FIGS. 4A and 4B are diagrams for illustrating the conceptual configuration of the present invention.
Figure 4B:
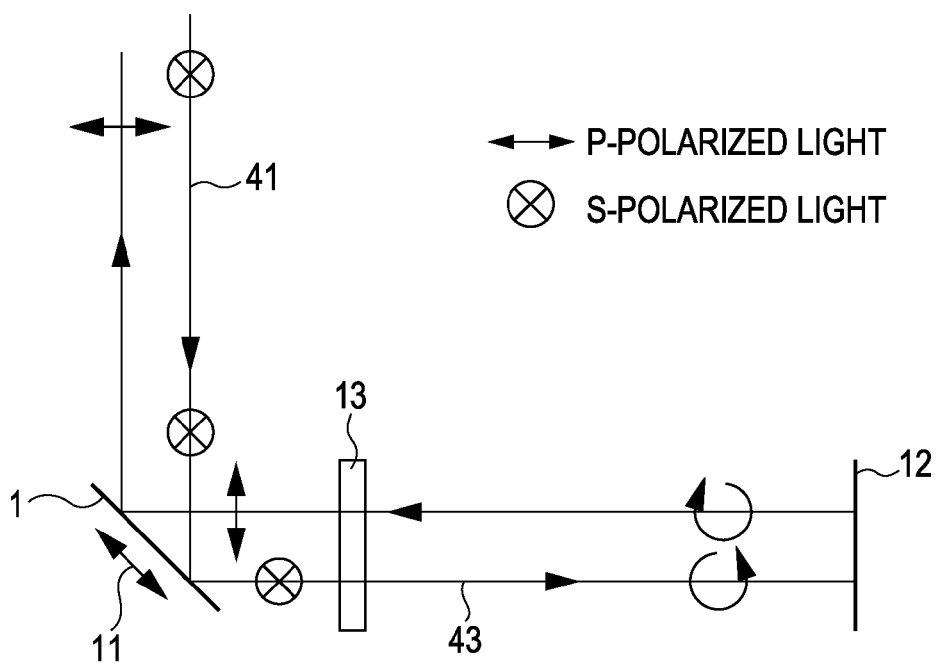

Next, the conceptual configuration of the present invention, which solves such a problem, will be described with reference to FIGS. 4A and 4B. In FIGS. 4A and 4B, reference numeral 1 denotes an SLM. In the present invention, as shown in FIGS. 4A and 4B, the polarization of light once modulated in the SLM1 is rotated 90°, and the light is incident on the SLM1 again and is modulated. Polarizers are not disposed in front of and behind the SLM1 to limit the polarized light component. Incident light 41 is incident on and is reflected by the SLM1, and the reflected light is folded by a mirror 12 and is incident on the SLM1 again. Between the SLM1 and the folding mirror 12, a quarter wave plate 13 is disposed so that light passes through it twice, outward and return.

The incident light 41 has both P- and S-polarized light components. First, the P-polarized light component (first polarized light component) shown in FIG. 4A will be discussed. The incident light 41 is P-polarized light having the same polarization direction as the modulation direction (intrinsic polarization direction) 11 of the SLM1. Therefore, when the light 41 is first incident on the SLM1, the light 41 is phase-modulated by a set amount of modulation and reflected by the SLM1. The reflected light 43 passes through the quarter wave plate 13 and becomes right-handed circularly polarized light, and it is reflected by the folding mirror 12 and becomes left-handed circularly polarized light. The light 43 passes through the quarter wave plate 13 again, becomes S-polarized light, and is incident on the SLM1 again. At this time, the polarization direction is perpendicular to the modulation direction 11 (intrinsic polarization direction, P-polarized light or S-polarized light can be modulated) of the SLM1, and therefore the light 43 is not modulated and is simply reflected.

Next, the S-polarized light component (second polarized light component) shown in FIG. 4B will be discussed. The incident light 41 is S-polarized light and differs by 90° from the modulation direction (intrinsic polarization direction) 11 of the SLM1. Therefore, when the light 41 is first incident on the SLM1, the light 41 is not modulated and is simply reflected. The reflected light 43 passes through the quarter wave plate 13 and becomes left-handed circularly polarized light, and it is reflected by the folding mirror 12 and becomes right-handed circularly polarized light. The light 43 passes through the quarter wave plate 13 again, becomes S-polarized light, and is incident on the SLM1 again. The polarization direction of the light 43 is the same as the modulation direction (intrinsic polarization direction) of the SLM1. This time, the light 43 is phase-modulated by a set amount of modulation and reflected by the SLM1. In FIGS. 4A and 4B, it looks as if the incident light and the reflected light traveled along different optical paths. However, this is for convenience of illustration. Actually, the incident light and the reflected light travel along the same optical path. Although the P-polarized light component and the S-polarized light component are separately shown, this is also for convenience of illustration. Actually, FIGS. 4A and 4B show events occurring in the same optical path at the same time. Due to this configuration, both polarized light components can be modulated with a single SLM1. Therefore, ignoring reflectivity, diffraction efficiency, and the like, loss of light quantity power used does not occur. By employing the unit of FIGS. 4A and 4B as the wavefront aberration correction unit 10 of FIG. 2, a bright and high S/N ratio image can be obtained even if wavefront aberration is corrected using a polarization-dependent SLM.

When a light beam is incident on the SLM1 again (reflected by the SLM1), each ray forming the light beam must be incident on the same incident point on the SLM1 as the incident point in its first incidence on the SLM1. If the incident point differ between the first and second incidence, the P-polarized light component and the S-polarized light component after the correction have different wavefronts because the same SLM1 performs the same modulation. Usually, a parallel light beam is incident on a wavefront aberration corrector. Therefore, when the amount of aberration to be corrected is small, the difference in incident point of each ray between the first and second incidence can be reduced by reducing the distance between the SLM1 and the folding mirror 12. However, when the amount of aberration to be corrected is large, the light beam is not parallel, and therefore a configuration such as that of FIGS. 4A and 4B cannot sufficiently correct aberration. The reason is that the P-polarized light component, which is modulated in the outward path, is properly corrected but the wavefront of the S-polarized light component that is incident on the SLM1 in the return path is changed to a wavefront different from the wavefront at the time when the P-polarized light component is incident on the SLM1. At this time, the S component is not properly corrected, and therefore the whole light beam is not sufficiently corrected.

Each ray is incident on the same position on the SLM1 in both the outward path and the return path only when the SLM1 surface at the time of the first incidence and the SLM1 surface at the time of the second incidence are optically conjugate to each other, are of the same magnification, and are in an erected image relationship. When they are in a conjugate relationship but the second incident surface is an inverted image relative to the first incident surface or they differ in magnification, each ray is not incident on the same position on the SLM1 again, and each polarized light component is differently modulated. In the present invention, in order to satisfy such conditions, a configuration such that the SLM1 surface in the outward path and the SLM1 surface in the return path are optically conjugate is provided in the folding optical path of the SLM1.

Although a case where light is incident on the SLM again has been described above, the present invention is not limited to this. It is also possible to modulate the P-polarized light component or the S-polarized light component of light, to rotate the light by 90 degrees, and then to cause the light to be incident on another SLM. In this case, two SLMs are provided.

EMBODIMENTS

Next, embodiments of the present invention will be described.

First Embodiment

Figure 1:
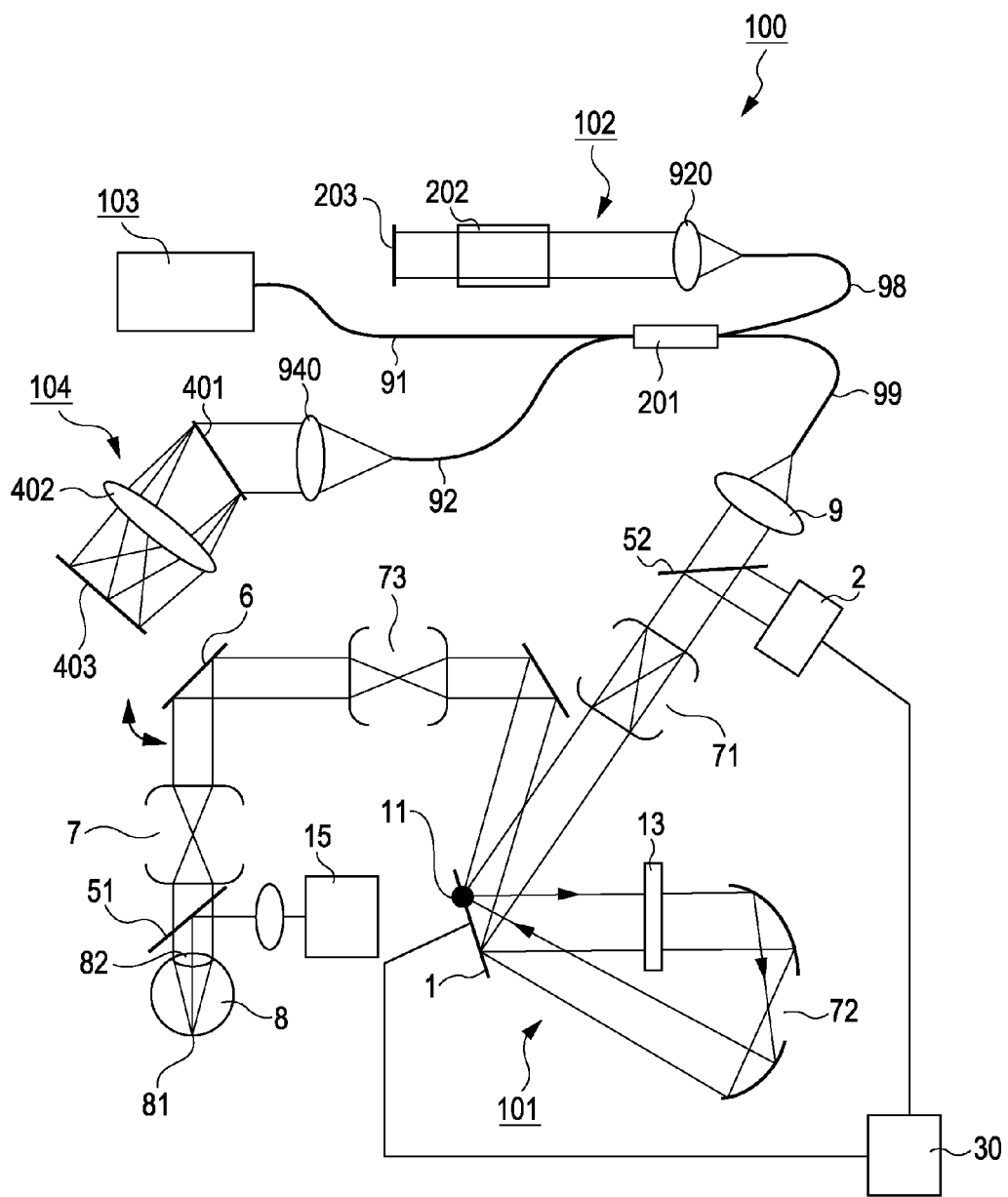
FIG. 1 is a conceptual diagram illustrating the configuration of an OCT in a first embodiment of the present invention.

In a first embodiment, with reference to FIG. 1, a description will be given of an optical image taking apparatus (an OCT in this embodiment) that examines a fundus to which the present invention is applied. The OCT of this embodiment is an SD-OCT (Spectral Domain OCT) including an observation system 101, a reference system 102, a light source 103, and a spectrometer 104. An SLD that emits light having a wavelength of 850 nm, which is poorly absorbed and poorly scattered by components of an eye, is used as the light source 103. Light emitted from the light source 103 propagates through a single-mode fiber 91 and is split by a coupler 201 into measurement light and reference light. The measurement light propagates through a fiber 99 to the observation system 101, and the reference light propagates through a fiber 98 to the reference system 102. After going out of the fiber 99 and being imaged onto the retina 81 of an eye 8 through an optical system of the observation system 101, the measurement light becomes backscattered or reflected light, goes back through the observation system 101, and re-enters the fiber 99.

On the other hand, after propagating through the fiber 98, the reference light is sent to the reference system 102, is collimated by a collimator lens 920, passes through dispersion compensating glass 202, is reflected by a reference mirror 203, passes through the reference system 102 again, and returns to the fiber 98. The lights returned to the fibers 98 and 99 are coupled by the coupler 201. The resultant light propagates through a fiber 92 to the spectrometer 104, goes out of the fiber end, and is collimated by a collimator lens 940. The collimated light is diffracted by a holographic grating 401 and is imaged by an imaging lens 402 onto a line sensor 403. The light is separated according to wavelength by the grating 401, and therefore a spectral intensity distribution is obtained in the line sensor 403. When the optical path length of the observation optical path from the branch point to the fundus is substantially equal to that of the reference optical path, interference fringes are produced in this spectral intensity distribution. By making this signal an intensity distribution relative to the wavenumber and then performing a Fourier transform thereon, an intensity distribution relative to the depth direction of the retina called "A scan data" is obtained. If light is scanned on the retina 81 by a scanner 6 and this intensity distribution is obtained in synchronization, a tomographic image of the retina 81 called "B scan image" is obtained.

The configuration in the observation system 101 will be described in more detail. First, wavefront aberration measurement light from the illumination light source 15 is reflected by the branch member 51, is incident on the eye 8, and is collected onto the measurement point on the retina 81. The wavelength of the light source 15 is 780 nm. The branch member 52 reflects part of light having this wavelength. The reflected or backscattered light (return light) from this point is influenced by the aberration of the ocular optical system, and the wavefront thereof is distorted. The light goes back the same optical path, passes through the pupil 82 to the optical system 71, is reflected by the branch member 52, and is incident on the HS sensor 2. The branch member 52 reflects 780 nm light and transmits 850 nm light. In the HS sensor 2, incident light is imaged by each subaperture onto the imaging element. From the displacement of the spots, wavefront aberration is calculated by the calculator 30. On the basis of it, the SLM1 is driven.

On the other hand, 850 nm illumination light (measurement light) for fundus examination going out of the fiber end 99 is collimated by the collimator lens 9, passes through the branch member 52, is enlarged or reduced and collimated by the optical system 71, and is incident on and reflected by the SLM1. The light is phase-modulated by the SLM1 and the wavefront thereof is changed. The light passes through the optical system 72, is reflected by the SLM1 again, passes through the optical system 73, the scanner mirror 6, and the optical system 7, and is incident on the eye 8. The pupil of the collimator lens, the SLM1, the scanner mirror 6, the pupil 81 of the eye are optically conjugate. This measurement light has a wavefront that compensates for the aberration of the ocular optical system when incident on the pupil 82. As a result, the light is in a good (low-aberration) state when collected onto the retina 81. The reflected or backscattered light from the irradiation point on the retina 81 is influenced by the aberration of the ocular optical system, and the wavefront thereof is distorted. The light goes back the same optical path, passes through the pupil 82 to the optical system 73, and is incident on the SLM1. The distorted wavefront is incident on the SLM1 twice, is corrected on the basis of the wavefront aberration calculated by the HS sensor 2, and is brought into a low-aberration state. The light passes through the optical system 71, the branch member 52, and the collimator lens 9, and is incident on the fiber 99. This feedback is repeated, the wavefront aberration converges toward a low state, and the reflected or backscattered light from the retina is well coupled into the fiber 99. Therefore, the tomographic image obtained by interference is high S/N, bright, and high-contrast.

The process of modulation in the SLM1 will be described in more detail. When the measurement light from the optical system 71 is first incident on the SLM1, only the P-polarized light component thereof is modulated. The light passes through the folding optical system 72 and is incident on the SLM1 again. In the folding optical path is disposed a half wave plate 13, where each polarized light component is rotated 90°. Therefore, when this light is incident on the SLM1 again, only a component that is S-polarized light in the outward path and is converted into P-polarized light by the wave plate in the return path is modulated. The optical system 72 includes two curved mirrors having the same focal length and is set such that the SLM surface in the outward path and the SLM surface in the return path are optically conjugate and of the same magnification. In order to form an erected image, a ray reflected at a point 11 on the SLM1 passes through the optical system 72 along the arrow and is then incident on this point 11 again. Therefore, in the above-described process, the P- and S-polarized light components are modulated once by the same amount. In this embodiment, due to such a configuration, conditions for each ray to be incident on the same position on the SLM1 in both the outward path and the return path are satisfied. In this optical system, the folding optical system is not a double-path optical system, and the incident angle on the SLM1 differs between the outward path and the return path. Therefore, the incident light from the fiber end 99 and the outgoing light heading to the eye differ in direction, and the loss due to use of a branch member can be avoided.

Second Embodiment

Figure 5:
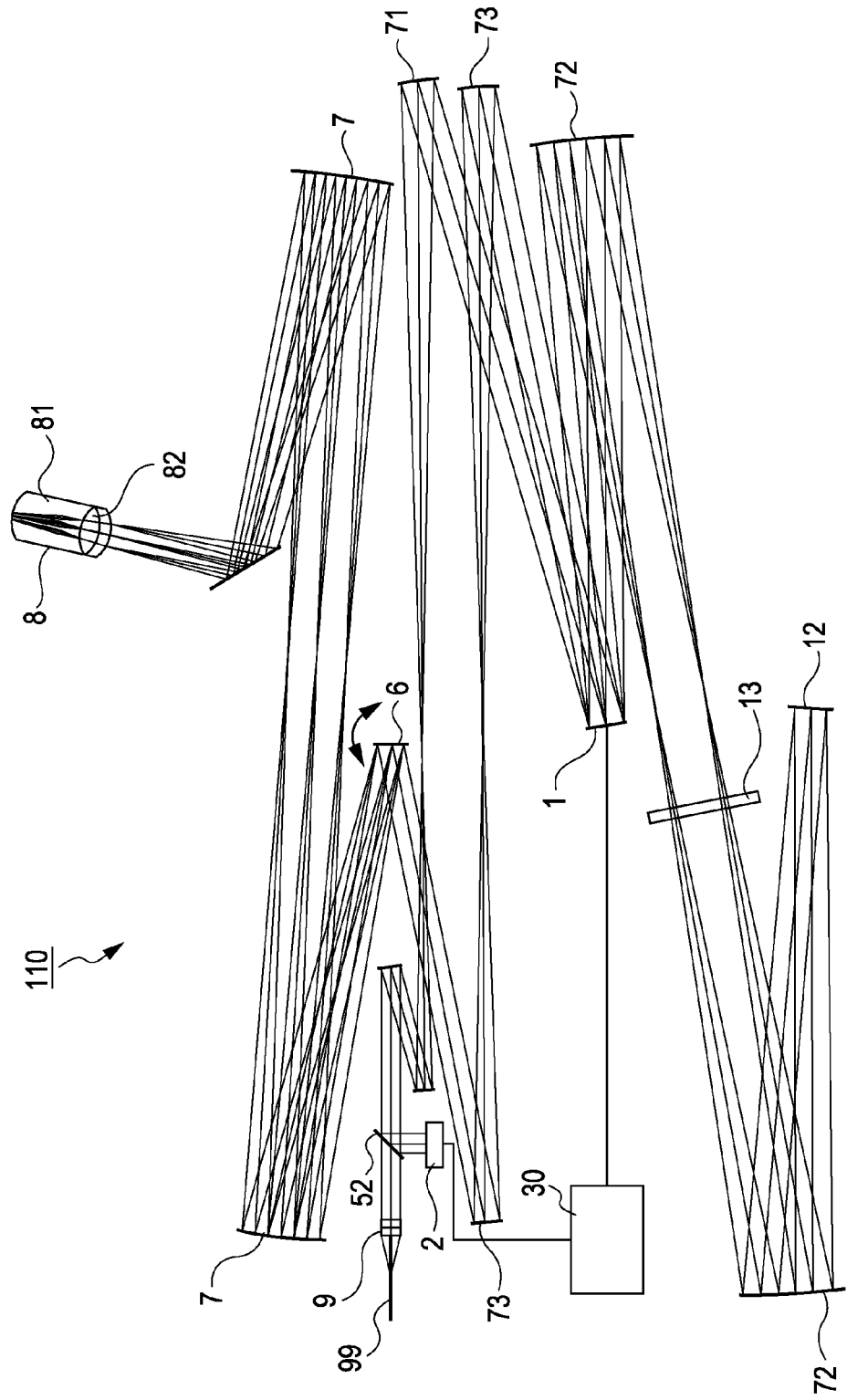
FIG. 5 is a conceptual diagram illustrating the configuration of an SLO in a second embodiment of the present invention.

In a second embodiment, with reference to FIG. 5, a description will be given of an optical image taking apparatus (an SLO in this embodiment) to which the present invention is applied. In FIG. 5, the same reference numerals are used to designate basically the same components as those in FIG. 1. In the first embodiment, a light source that emits light for aberration measurement is separately provided. In this embodiment, illumination light (measurement light) for fundus examination is also used as wavefront aberration measurement light. In the SLO of this embodiment denoted by reference numeral 110 in FIG. 5, illumination (measurement) light from a light source (not shown) is coupled into a single-mode fiber 99, propagates therethrough, becomes diverging light after going out of the exit end, is collimated by a collimator lens 9, and passes through a branch member 52. The core diameter of the fiber is 5 μm, the focal length of the collimator lens is about 10 mm, and the diameter of the collimated light is about 4 mm. After that, the light is converted into parallel light of about 8 mm by an optical system 71 and is incident on an SLM1. At this time, the SLM1 is not modulated, and the wavefront of the parallel light is not changed. The parallel light passes through an optical system 72, is incident on and reflected by the SLM1 again, passes through an optical system 73, a scanner mirror 6, and an optical system 7, and is incident on an eye 8. The pupil of the collimator lens, the SLM1, the scanner mirror 6, the pupil 82 of the eye, and a flat mirror 12 for folding are optically conjugate. The diameter of light incident on the scanner mirror 6 is set to 6 mm, and the diameter of light incident on the eye 8 is also set to 6 mm. The surface normal of the mirror 12 is inclined at 4° to the principal ray of the incident light. The reflected light is at an angle different from that of the incident light. The reflected light passes through the optical system 73 again, and is incident on the SLM1 again. At this time, the mirror 12 and the SLM1 are optically conjugate and of the same magnification. Therefore, the incident light on the SLM1 in the outward path and the incident light on the SLM1 in the return path differ in angle and are incident on the same position.

The measurement light incident on the eye 8 is collected onto the retina 81. The reflected or backscattered light from this point is influenced by the aberration of the ocular optical system, and the wavefront thereof is disordered. The light goes back the same optical path and passes through the pupil 82 to the optical system 71. Part of the light is reflected by the branch member 52 and is incident on the HS sensor 2. From the displacement of spots imaged by each subaperture onto the imaging element, wavefront aberration is calculated by a calculator 30. On the basis of it, the SLM1 is driven. By repeating this feedback, the measurement light to the eye has a wavefront that compensates for the aberration of the ocular optical system when incident on the pupil 82. As a result, the light is in a good (low-aberration) state when collected onto the retina 81.

The reflected or backscattered light (return light) from the irradiation point on the retina is influenced by the aberration of the ocular optical system again, and the wavefront thereof is disordered. The light goes back the same optical path, passes through the pupil 82 to the optical system 73, and is incident on the SLM1. The distorted wavefront is corrected by the SLM1 and is brought into a low-aberration state. The light passes through the branch member 52 and the collimator lens 9 and is incident on the fiber 99. After propagating through the fiber 99, the light is split by a branch member (not shown) beyond the fiber 99 and is incident on a photoelectric sensor such as an avalanche photodiode, where the quantity of light is measured. By synchronizing this with a scanner mirror that performs two-dimensional scan, a two-dimensional image of the retina is formed. At this time, the reflected or backscattered light from the retina is well coupled into the fiber 99. Therefore, the two-dimensional retina image obtained is high S/N, bright, and high-contrast.

The process of modulation in the SLM1 will be described in more detail. When the light from the optical system 71 is first incident on the SLM1, only the P-polarized light component thereof is modulated. The light passes through the folding optical system 72 and is incident on the SLM1 again. A quarter wave plate 13 is disposed in the folding optical path. Passing through the quarter wave plate 13 twice (outward and return), each polarized light component is rotated by 90°. Therefore, when this light is incident on the SLM1 again, only a component that is S-polarized light component in the outward path and is converted into P-polarized light by the wave plate in the return path is modulated. In the above-described process, the P- and S-polarized light components are modulated once by the same amount.

Also in this folding optical system 72, the incident angle on the SLM1 differs between the outward path and the return path. Therefore, the incident light (measurement light) from the fiber end 99 and the outgoing light (return light) heading to the eye differ in direction, and the loss due to use of a branch member can be avoided. In addition, because the outward path and the return path share a common optical system, the space can be saved. In the above-described SLO 110, low-order aberrations such as astigmatism and defocus may be corrected by the SLM1. However, when the amount of correction is larger than 5D or when the wavelength interval of a light source used is about 100 nm, the decrease in diffraction efficiency and chromatic aberration are significant, and in some cases, desired correction performance cannot be obtained. In this case, instead of a flat mirror, a deformable mirror may be used as the folding mirror 12. By using a deformable mirror that has a small number of actuators and cannot reproduce a high-order curved surface but is capable of a large amount of correction on a low-order curved surface, low-order aberrations are corrected, and third- or higher-order aberrations are corrected by the SLM1. The amplitude of high-order aberrations is generally small. Therefore, the amount of modulation of the LCOS1 can be reduced, and problems caused by a large amount of modulation can be prevented.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-244961 filed Oct. 23, 2009, which is hereby incorporated by reference herein in its entirety.

What is claimed is:

1. An adaptive optics apparatus comprising:
   a light modulating unit configured to modulate light in a polarization direction of one of two polarized light components, wherein the light is emitted from a light source; and
   a changing unit configured to rotate a polarization direction of the modulated light by 90 degrees;
   wherein
   the light modulating unit is configured to modulate the light from the changing unit so as to modulate the light in a polarization direction of the other of the two polarized light components, and
   two wave surfaces of the light at the time of modulating the light in the two polarized light components are in an optically conjugate relationship and in an erected image relationship.

2. The adaptive optics apparatus according to claim 1, further comprising an aberration measuring unit configured to measure aberration of a measurement object, wherein the light modulating units are disposed at a position optically conjugate to the aberration measuring unit, and the two wave surfaces are of the same magnification.

3. The adaptive optics apparatus according to claim 2, wherein the measurement object is an eye under examination, the aberration occurs in an anterior segment of the eye under examination, and the light modulating units are disposed at a position optically conjugate to the anterior segment.

4. The adaptive optics apparatus according to claim 2, wherein light used when the aberration measuring unit measures the aberration and light used when an image of the measurement object is obtained are emitted from different light sources.

5. The adaptive optics apparatus according to claim 1, further comprising a unit configured to reflect the light rotated by 90 degrees by the changing unit and to irradiate the light modulating unit therewith, wherein two incident lights on the light modulating unit at the time of modulating the light in the two polarized light components differ in angle.

6. The adaptive optics apparatus according to claim 1, further comprising an irradiating unit configured to irradiate a measurement object with the light modulated by the light modulating unit, wherein the light modulating unit modulates return light from the measurement object irradiated by the irradiating unit in one of the two polarized light components, the changing unit rotates a polarization direction of the light modulated by 90 degrees, and the light modulating unit modulates the light from the changing unit so as to modulate the light in a polarization direction of the other of the two polarized light components.

7. An image taking apparatus comprising:
the adaptive optics apparatus according to claim 1;
an irradiating unit configured to irradiate a measurement object with the light modulated by the light modulating unit; and
an image obtaining unit configured to obtain an image of the measurement object on the basis of return light from the measurement object irradiated by the irradiating unit.

8. The image taking apparatus according to claim 7, further comprising a separating unit configured to separate the light from the light source into light to be incident on the light modulating unit and reference light, wherein the image obtaining unit obtains a tomographic image of the measurement object on the basis of interfering light of the return light from the measurement object irradiated by the irradiating unit and the reference light.

9. An adaptive optics method comprising:
a light modulating step of modulating light in a polarization direction of one of two polarized light components, wherein the light is emitted from a light source; and
a changing step of rotating a polarization direction of the modulated light by 90 degrees;
wherein
the light modulating step modulates the light from the changing step, so as to modulate the light in a polarization direction of the other of the two polarized light components, and
two wave surfaces of the light at the time of modulating the light in the two polarized light components are in an optically conjugate relationship and in an erected image relationship.

* * * * *